(12) United States Patent
Yano

(10) Patent No.: US 7,653,498 B2
(45) Date of Patent: Jan. 26, 2010

(54) APPARATUS FOR AND METHOD OF CALCULATING MANY-BODY PROBLEM

(75) Inventor: Yuichi Yano, Minato-ku (JP)

(73) Assignee: NEC Corporation, Tokyo (JP)

( * ) Notice: Subject to any disclaimer, the term of this patent is extended or adjusted under 35 U.S.C. 154(b) by 420 days.

(21) Appl. No.: 11/554,287

(22) Filed: Oct. 30, 2006

(65) Prior Publication Data

US 2007/0100590 A1    May 3, 2007

(30) Foreign Application Priority Data

Oct. 31, 2005    (JP)    ............... 2005-315999

(51) Int. Cl.
*G01N 31/00* (2006.01)
*G01L 1/00* (2006.01)

(52) U.S. Cl. .................. 702/33; 702/30; 702/31; 702/41; 703/2

(58) Field of Classification Search ........... 702/22, 702/27–32, 41; 703/2, 11, 12
See application file for complete search history.

(56) References Cited

U.S. PATENT DOCUMENTS

2003/0014231 A1* 1/2003 Zhou et al. ................. 703/11

FOREIGN PATENT DOCUMENTS

| JP | 4-77853 A | 3/1992 |
| JP | 04077853 A * | 3/1992 |
| JP | 6-223052 A | 8/1994 |
| JP | 6-231114 A | 8/1994 |
| JP | 6-231115 A | 8/1994 |
| JP | 06223052 A * | 8/1994 |
| JP | 8-285757 A | 11/1996 |
| JP | 9-251449 A | 9/1997 |
| JP | 2001-236342 A | 8/2001 |
| JP | 2001236342 A * | 8/2001 |

OTHER PUBLICATIONS

Masaaki Takai et al., "Parallel processing of the molecular dynamics method using dynamic grouping of particles" The Institute of Electronics, Information and Communication Engineers Abstracts, Jun. 25, 1999, pp. 711-717, vol. J82-D-I, No. 6, The Institute of Electronics, Information and Communication Engineers, Japan.

(Continued)

*Primary Examiner*—Eliseo Ramos Feliciano
*Assistant Examiner*—Phuong Huynh
(74) *Attorney, Agent, or Firm*—Sughrue Mion, PLLC

(57) ABSTRACT

An address generator holds a cell list of cell data of a central cell containing a central particle and a predetermined number of surrounding cells located around the central cell in a system. The address generator designates particle data of a central particle and particles that are present around the central particle, from the cell data of the cell list, and successively updates the cell list according to predetermined rules until all the cells in the system will serve as a central cell. A memory controller reads particle data of particles that are used to calculate short-range forces that have been designated by the address generator, from a storage unit, and transfers the read particle data to a force calculator for calculating short-range forces between particles.

8 Claims, 6 Drawing Sheets

OTHER PUBLICATIONS

Taishi Shimizu et al, "Parallel molecular dynamic stencils: comparison of parallelization technique and cutoff technique", The Japan Society for Computational Engineering and Science Abstracts, pp. 229-232, vol. 6, No. 1, The Japan Society for Computational Engineering and Science, Japan.

* cited by examiner

APPARATUS FOR AND METHOD OF CALCULATING MANY-BODY PROBLEM

This application is based upon and claims the benefit of priority from Japanese Patent Application No. 2005-315999 filed on Oct. 31, 2005, the content of which is incorporated by reference.

BACKGROUND OF THE INVENTION

1. Field of the Invention

The present invention relates to an apparatus for and a method of calculating a many-body problem to calculate forces acting between particles in a system.

2. Description of the Related Art

For solving many-body problems in various fields including molecular dynamics, it is necessary to calculate forces acting between many particles in a system in order to explain properties of the system and to predict changes of the system. However, calculating forces that act between all the particles requires an enormous computational effort. Therefore, a method has been implemented to reduce the amount of calculation according to which the cut-off distance is determined, depending on the level of calculation accuracy that is required, and only the forces that act between a particular particle and other particles that are present within the cut-off distance, are calculated.

However, the conventional process needs to determine the distances between the particular particle and to all the other particles in the system and compare the distances within the cut-off distance in order to check if each of the particles is present in the cut-off distance or not. Generally, a system containing N particles requires more calculations since N is greater because the amount of necessary calculations increases in proportion to $N^2$. Heretofore, a dedicated hardware-implemented calculating apparatus has been employed to calculate short-range forces such as Van der Waals forces between particles.

For efficiently calculating short-range forces between particles, it is desirable to efficiently select particles that are present near a particular particle so as to reduce the amount of calculations of distances between the particles. For example, JP-A No. 2001-236342 discloses a process of dividing a space (system), to be calculated, containing a number of particles into a plurality of subcells each in a rectangular parallelepiped shape, and efficiently selecting particles to be calculated for short-range forces based on the proximity relationship between the subcells.

A many-body problem calculating apparatus disclosed in JP-A No. 2001-236342 comprises a particle coordinate memory for storing the coordinates of particles and an index memory for storing the addresses of the particle coordinate memory which has stored the coordinates of the particles. The addresses of the particle coordinate memory which correspond to the respective particles are stored in the index memory in relation to the subcells that are assigned based on the coordinates of the particles. When the short-range forces between the particles are to be calculated, a subcell in which a particular particle is present and a subcell that is present near that subcell are designated based on the proximity relationship between the subcells, the particles belonging to the designated subcells are selected for calculating short-range forces therebetween, and the coordinates of the selected particles are acquired from the particle coordinate memory.

Consequently, it is necessary for information about the coordinates of all the particles contained in the system and information about the subcells to which the particles belong to be stored in memory. Since there are as many items of information about the subcells as the number of the particles, the data stored in memory are enormous. The many-body problem calculating apparatus needs to have a memory having a huge storage capacity. Therefore, the many-body problem calculating apparatus and an address generator, which the many-body problem calculating apparatus has, for selecting particles to be calculated and for particles present therearound, are highly costly to manufacture.

SUMMARY OF THE INVENTION

It is therefore an object of the present invention to provide an apparatus for and a method of calculating a many-body problem by efficiently selecting particles which are present near a particular particle to reduce the amount of calculations of short-range forces between particles and also to lower the cost of the apparatus.

According to the present invention, a many-body problem calculating apparatus has an address generator for holding a cell list of cell data of a central cell containing a central particle and a predetermined number of surrounding cells around the central cell in a system, for designating particle data of a central particle and particles that are present around the central particle, from the cell data of the cell list, and for successively updating the cell list according to predetermined rules until all the cells in the system will serve as a central cell, and a memory controller for reading particle data of particles that are used to calculate short-range forces that have been designated by the address generator, from a storage unit, which stores particle data of all particles contained in the system and cell data of all cells, and for transferring the read particle data to a force calculator for calculating short-range forces between particles.

With the above many-body problem calculating apparatus, since the length of a side of each cell may be determined optimally to efficiently select a central particle and particles that are present within a cut-off distance, the calculation of distances between unwanted particles is eliminated. Furthermore, because the cell list is successively updated according to the predetermined rules until all the cells of the system will serve as a central cell, the cell list is autonomously updated in the many-body problem calculating apparatus, and hence short-range forces acting on the particles in the system can be efficiently calculated without the need for an external apparatus. The many-body calculating apparatus employs only information that will identify a cell and the number of particles contained in the cell as cell data. Consequently, the amount of data stored in the storage unit is smaller than in the case of conventional many-body calculating apparatuses. The storage unit of the many-body calculating apparatus may thus have a reduced storage capacity, and hence the many-body calculating apparatus may be less costly to manufacture.

The above add other objects, features, and advantages of the present invention will become apparent from the following description with reference to the accompanying drawings which illustrate examples of the present invention.

DETAILED DESCRIPTION OF THE PREFERRED EMBODIMENT

Figure 1:
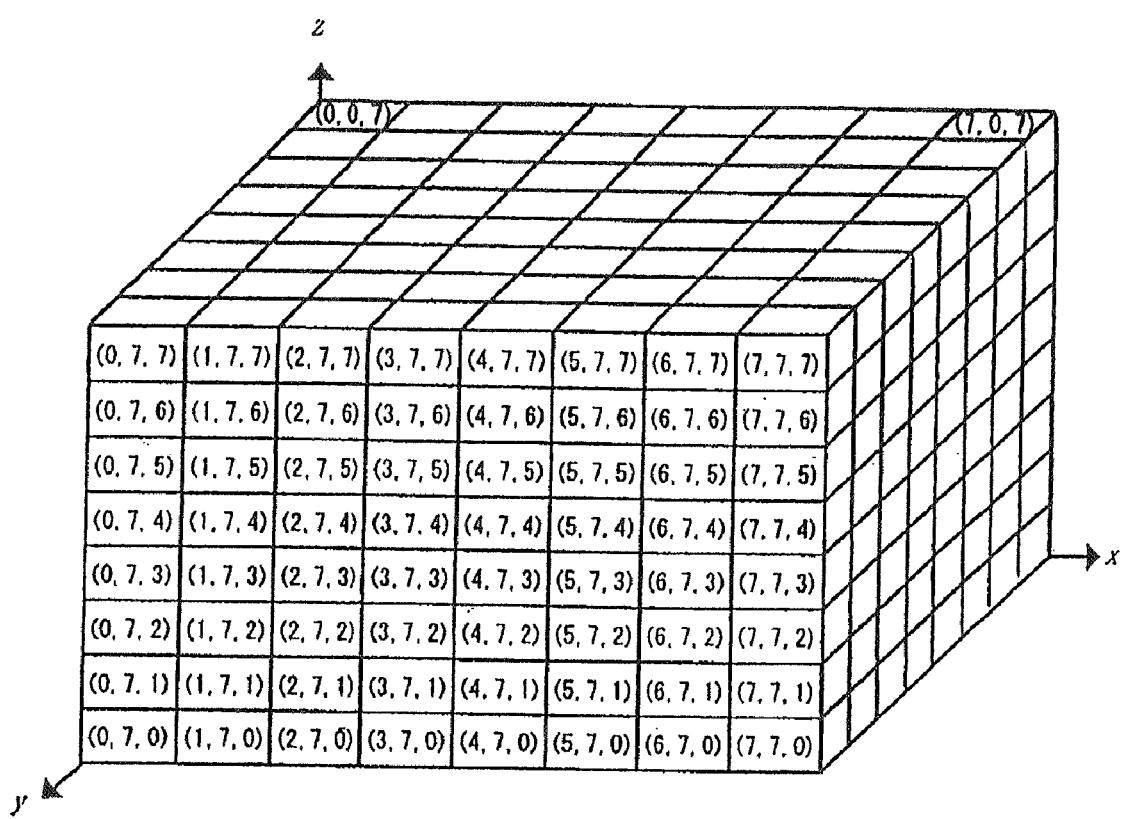
FIG. 1 is a schematic perspective view showing a system divided into a plurality of cells.

According to the present invention, a system to be calculated is divided into a plurality of spaces as cells, as shown in FIG. 1. For calculating a force acting on a particular particle (hereinafter referred to as "central particle"), a cell (hereinafter referred to as "central cell") containing the central particle and cells (hereinafter referred to as "surrounding cells") surrounding the central cell are designated. Then, distances between the central particle and other particles contained in the central cell, distances between the central particle and all particles contained in the surrounding cells, and forces (short-range forces) acting between the particles are calculated. Specifically, forces acting between particles are calculated for 3×3×3 (the numbers of cells in x, y, and z directions)=27 cells or 5×5×5=125 cells. With respect to particles contained in the other cells, the calculation of short-range forces may be omitted or may be performed according to a known approximation process depending on the level of calculation accuracy that is required.

FIG. 1 shows a system which is divided into 8×8×8=512 cells with corresponding coordinates (x, y, z) being assigned thereto.

The number of cells wherein forces acting between particles are calculated is not limited to 27 or 125, but may be any value, e.g., 7×7×7=343, insofar as the number of cells in each of the x, y, and z directions is an odd number. However, if the number of cells to be calculated increases, then the storage capacity of a list memory, to be described later, needs to be increased. Therefore, the number of cells, wherein forces acting between particles are calculated, should preferably be 27 or 125.

The many-body problem calculating apparatus according to the present invention has a list memory for temporarily storing information about 27 or 125 cells. The many-body problem calculating apparatus selects a central cell and surrounding cells to be calculated from the list memory, successively reads information about the particles contained in the selected cells, and calculates distances between the particles and short-range forces acting between the particles. Information about each cell will hereinafter be referred to as cell data, a plurality of cell data held by the list memory as a cell list, and information about each particle as particle data.

The particle data of all particles contained in the system and the cell data of all cells making up the system are stored in advance in a storage unit of the many-body problem calculating apparatus before short-range forces acting between particles are calculated. The particle data are data, such as positional coordinates (x, y, z) and an electric charge Q of each particle, required to calculate short-range forces (non-bonding forces) acting between particles. The cell data represent information to identify a cell, e.g., the address of the storage unit which stores a central particle (hereinafter referred to as "leading particle") to be first selected in the cell as a particle to be calculated, and the number of particles contained in the cell. The information to identify a cell is not limited to the address of the storage unit which stores the leading particle, but may be any information that is capable of identifying each cell. For example, the coordinate data of the leading particle may be used, or an identification number, a name, or the like assigned to each cell may be used.

According to the present invention, when the calculation of short-range forces acting between each of all particles contained in the central cell and other particles contained in the central cell, and between each of all particles contained in the central cell and all particles contained in the surrounding cells (particles that are present around central particles therein), is finished, the cell adjacent to the central cell is defined as a new central cell, and cells surrounding the new central cell are defined as new surrounding cells. Then, the cell list is updated according to the central cell and the surrounding cells that have been newly defined, cell data are successively read based on the updated cell list, and short-range forces acting between each of all particles contained in the newly defined central cell and other particles contained in the newly defined central cell, and between each of all particles contained in the newly defined central cell and all particles contained in the surrounding cells are calculated. The same process is repeatedly performed until all the cells, making up the system will serve as a central cell, thereby calculating short-range forces acting between all the particles contained in the system.

Figure 2:
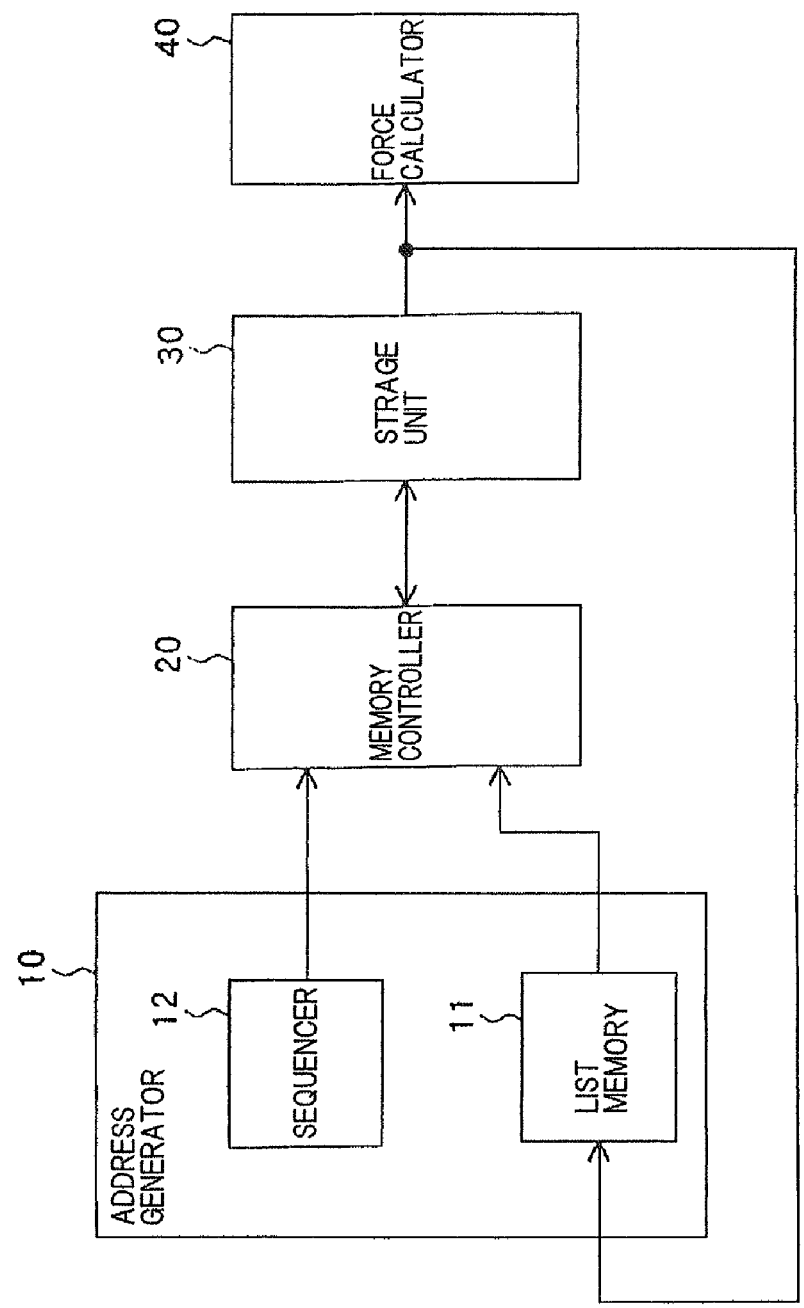
FIG. 2 is a block diagram showing an arrangement of a many-body problem calculating apparatus according to the present invention.

As shown in FIG. 2, the many-body problem calculating apparatus according to the present invention comprises force calculator 40 for calculating short-range forces using particle data, storage unit 30 for storing particle data of all particles contained in a system to be calculated and cell data of all cells contained in the system, address generator 10 for holding a cell list representing cell data of a central cell containing a central particle and a predetermined number of surrounding cells that are present around the central cell, for designating particle data of the central particle and particles that are present around the central particle, between which to calculate short-range forces, from the cell data represented by the cell list, and for successively updating the cell list according to predetermined rules until all the cells in the system will serve as a central cell each time the calculation of short-range forces between each of all the particles in the central cell and the particles that are present around the particle is completed, and memory controller 20 for reading particle data of particles that are used to calculate short-range forces that have been designated by address generator 10, from storage unit 30, and for transferring the read particle data to force calculator 40.

Address generator 10 comprises list memory 11 for temporarily holding the cell list and sequencer 12 for indicating particle data to be transferred from storage unit 30 to force calculator 40, according to the cell list held by list memory 11, to memory controller 20, and for updating the cell list held by list memory 11 according to the predetermined rules.

Sequencer 12 has a plurality of counters, a plurality of registers, a plurality of timers, etc. required for data processing, e.g., first through third counters for counting the number of times that a central cell has moved respectively in the x, y, and z directions in the system, a fourth counter for counting the number of particles in a central cell, a fifth counter for counting the number of cells registered in the cell list, a central cell data storage unit for temporarily storing the cell data of a central cell, and registers for holding read addresses to read cell data from list memory 11 and for holding write addresses to store cell data in list memory 11.

Storage unit 30 stores in advance particle data of all particles contained in a system to be calculated and cell data of all cells contained in the system, which are supplied by the operator or by an information processing apparatus such as a computer or the like. Each of address generators 10 and memory controller 20 may comprise a logic circuit, a memory, etc. Specifically, each of address generators 10 and memory controller 20 may have a CPU (or DSP) and a memory, and the CPU (or DSP) may run a program stored in the memory to realize the functions of each of address generators 10 and memory controller 20. Force calculator 40 may be a calculation-dedicated computer comprising a CPU, a DSP, a logic circuit, a memory, etc.

When the many-body problem calculating apparatus shown in FIG. 2 is used to calculate short-range forces between particles in a system, sequencer 12 controls memory controller 29 to read cell data of a central cell containing a central particle to be calculated and cell data of surrounding cells around the central cell from storage unit 30, and registers the read cell data as a cell list in list memory 11.

When the cell list is registered in list memory 11, memory controller 20 reads the particle data of a leading particle contained in the central cell which is designated by the cell list, and transfers the read particle data to force calculator 40, according to instructions from sequencer 12.

Then, according to instructions from sequencer 12, memory controller 20 reads cell data of a particular cell (the central cell or one of the surrounding cells) from among the cells registered in the cell list in storage unit 30, reads particles data of all particles contained in the cell, and transfers the read particle data to force calculator 40. Force calculator 40 calculates short-range forces acting on the leading particle by using the particle data of the leading particle that has been transferred previously and the particle data that has been transferred subsequently.

When the reading of the particle data of all the particles contained in the initially read cell is finished, memory controller 20 reads the cell data of the next cell registered in the cell list, reads particle data of all particles contained in the next cell, and transfers the read particle data to force calculator 40, according to instructions from sequencer 12. Force calculator 40 calculates short-range forces acting on the leading particle by using the particle data of the leading particle that has been transferred previously and the particle data that has been transferred subsequently.

The same process is subsequently repeated to read particle data of all particles contained in each of all the cells registered in the cell list, and to transfer the read particle data to force calculator 40. When reading of the particle data of all the cells registered in the cell list is finished, memory controller 20 reads particle the data of a particle (central particle) to be calculated next, contained in the central cell, from storage unit 30, and transfers the read particle data to force calculator 40, according to instructions from sequencer 12. Force calculator 40 calculates short-range forces acting on the central particle that has been read next from all the particles contained in each cell (the central cell or each of the surrounding cells).

When force calculator 40 finishes the calculation of short-range forces acting on all the particles contained in the central cell, sequencer 12 defines a cell adjacent to the central cell as a new central cell, and defines cells surrounding the new central cell as new surrounding cells. Sequencer 12 controls memory controller 20 to read cell data of the new central cells and the new surrounding cells from storage unit 30, and to store the read cell data in list memory 11, thereby updating the cell list.

Subsequently, short-range forces acting on all the particles contained in the newly defined central cell are calculated, and the cell list is repeatedly updated until all the cells making up the system will serve as a central cell, thereby calculating short-range forces acting between all the particles contained in the system.

According to the present invention, since the length of a side of each cell may be determined optimally to efficiently select a central particle and particles that are present within a cut-off distance, the calculation of distances between unwanted particles is eliminated. Furthermore, because the cell list is successively updated according to the predetermined rules until all the cells of the system will serve as a central cell, the cell list is autonomously updated in the many-body problem calculating apparatus, and hence short-range forces acting on the particles in the system can efficiently be calculated without the need for an external apparatus.

A processing sequence of the sequencer will be described below with reference to FIGS. 3 through 6.

It is assumed below that particle data of all the particles contained in a system to be calculated and cell data of the system are stored in storage unit 30. It is also assumed that short-range forces acting between particles are calculated for 3×3×3 cells (the numbers of cells in x, y, and z directions)=27 cells, and cell data of 27 cells are stored as a cell list in list memory 11.

Figure 3:
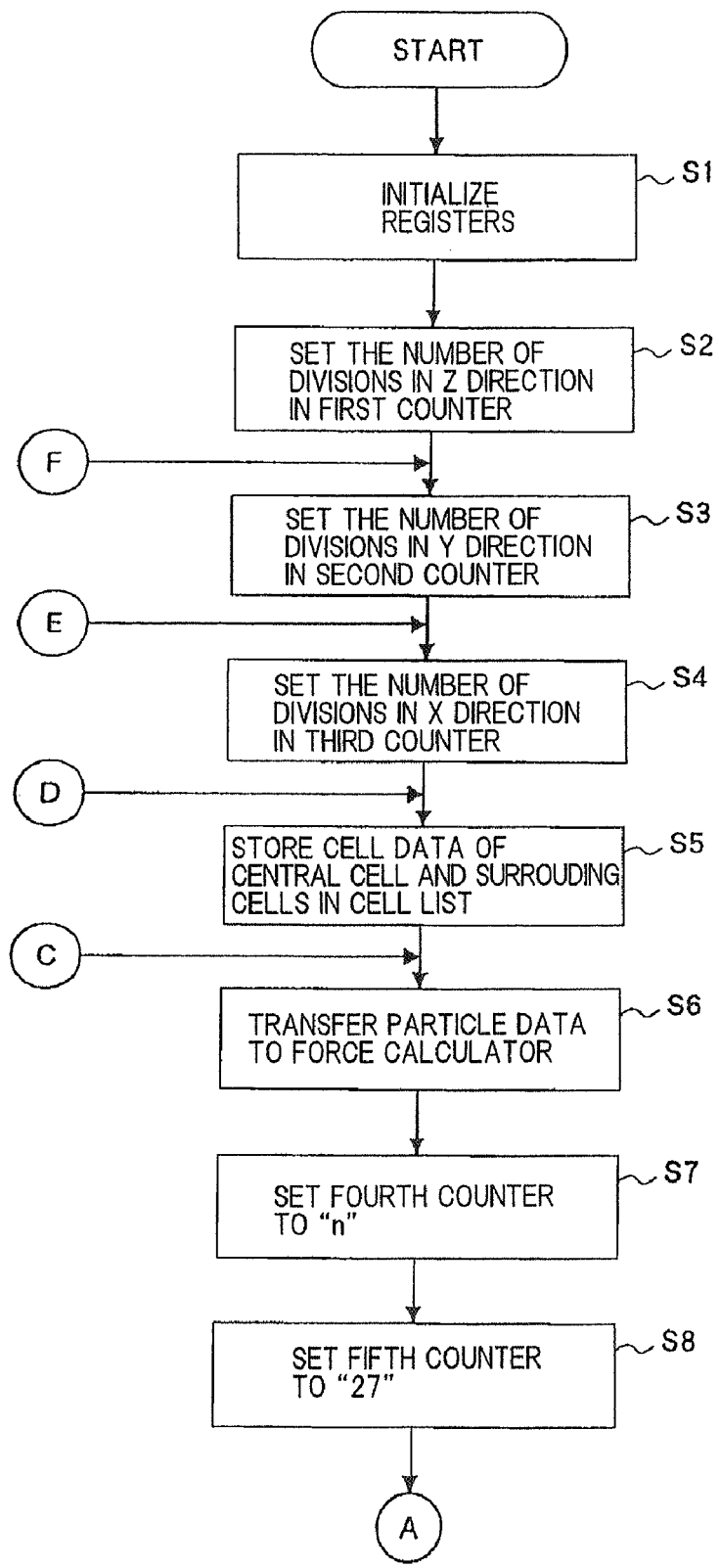
FIG. 3 is a flowchart of a portion of a processing sequence of a sequencer shown in FIG. 2.
Figure 4:
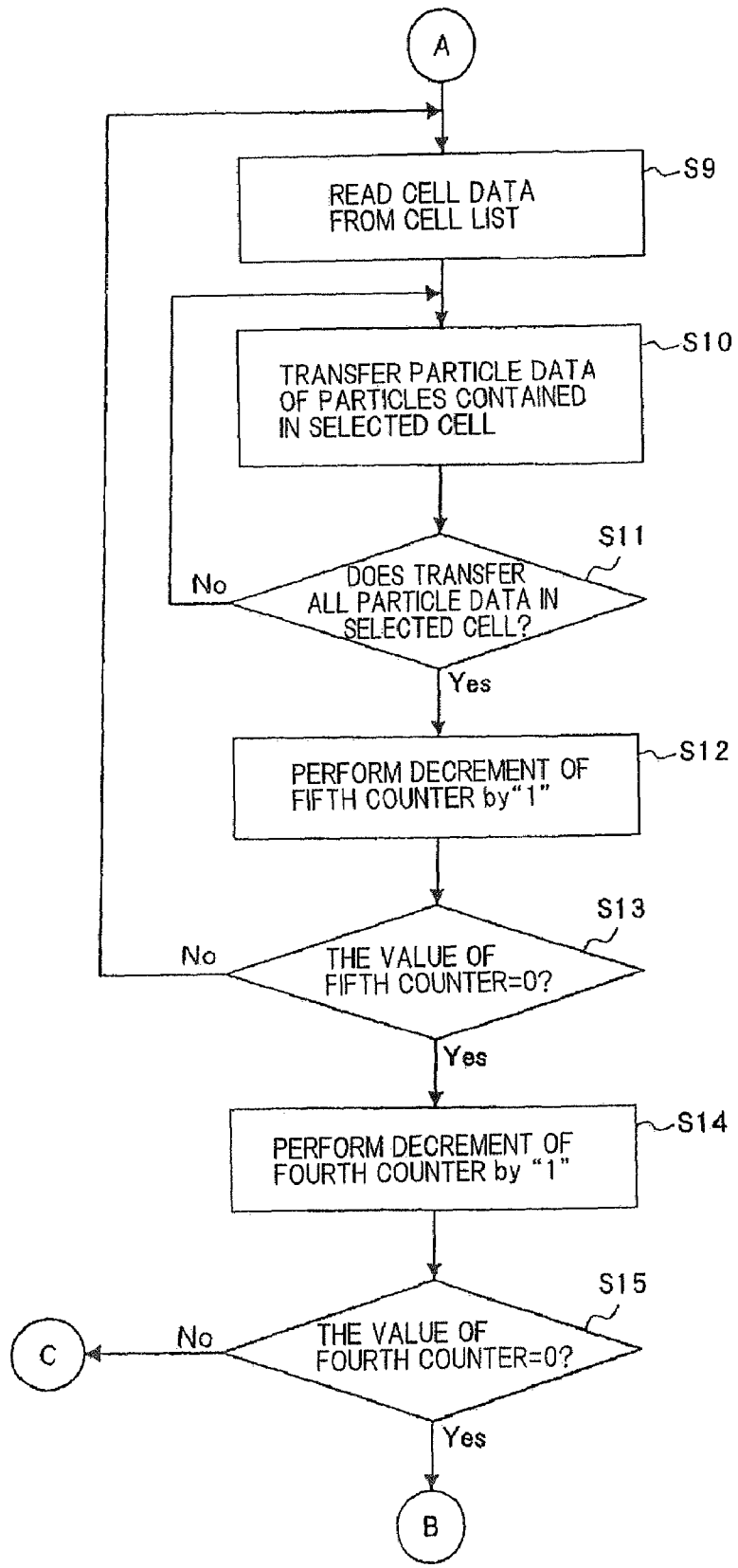
FIG. 4 is a flowchart of another portion of the processing sequence of the sequencer shown in FIG. 2.
Figure 5:
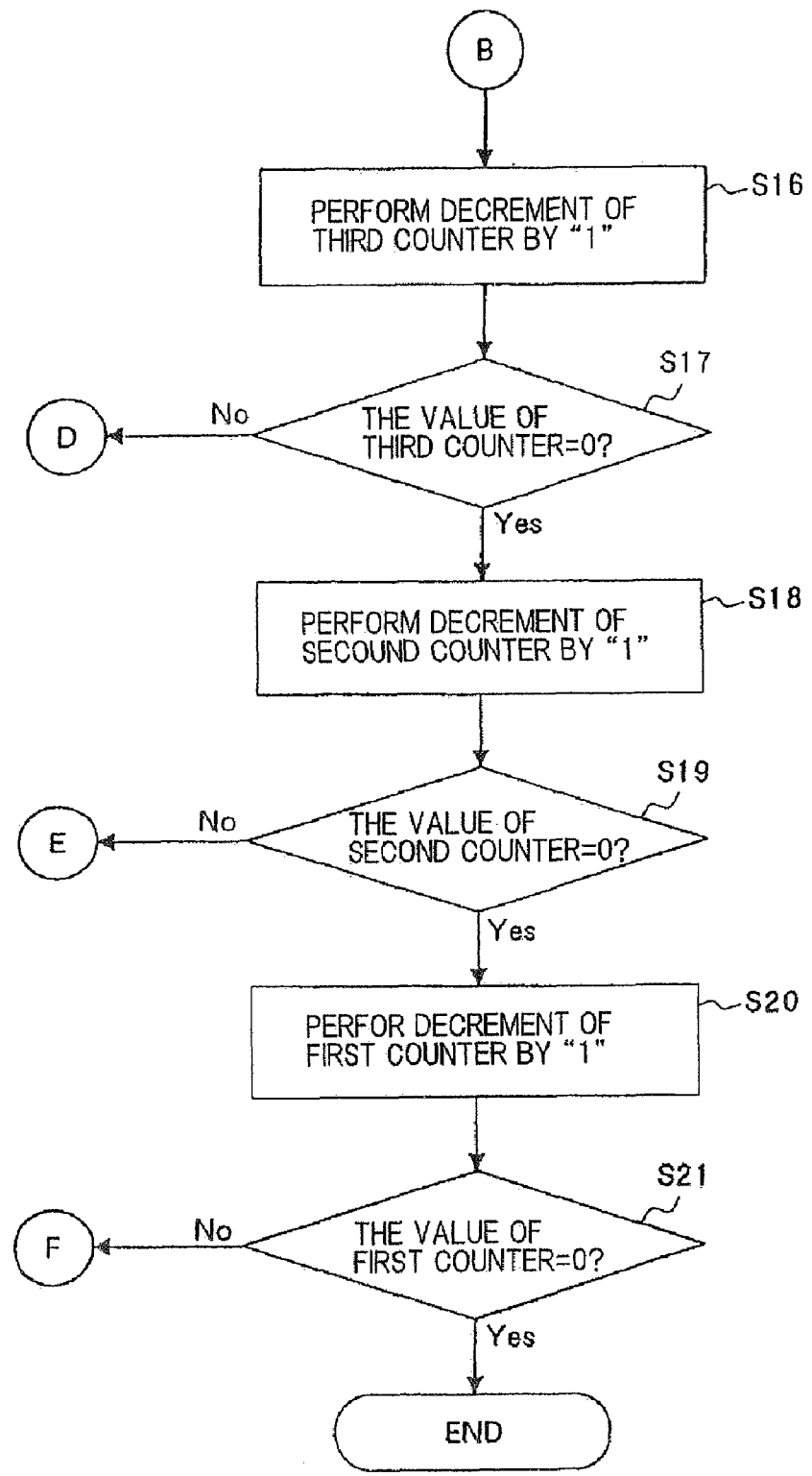
FIG. 5 is a flowchart of still another portion of the processing sequence of the sequencer shown in FIG. 2.

As shown in FIGS. 3 through 5, sequencer 12 of address generator 10 initializes the values of registers that will hold a read address in order to read cell data from list memory 11, and that will hold a write address in order to store cell data in list memory 11, and sets "0" in the registers (step S1).

Then, sequencer 12 sets the number of divisions in the x, y, and z directions (the number of cells in the x, y, and z directions) depending on the cell configuration of the system, in the first through third counters (steps S2 through S4). Specifically, the number of divisions in the x direction is set in the first counter (step S2), the number of divisions in the y direction is set in the second counter (step S3), and the number of divisions in the z direction is set in the third counter (step S4).

Then, sequencer 12 controls memory controller 20 to read cell data of a central cell to be first calculated for the short-range forces and cell data of surrounding cells that are present around the central cell from storage unit 30, and to store the read cell data in list memory 11. At this time, cell data of 9 cells in either one of the x, y, and z directions are read from storage unit 30. For example, if cell data are to be read in the x direction, they are read with respect to 1×3×3 cells. If cell data are to be read in the y direction, they are read with respect to 3×1×3 cells. If cell data are to be read in the z direction, they are read with respect to 3×3×1 cells. The value of the register of sequencer 12 which stores the write address for list memory 11 is incremented by "9". When the cell data of all cells to be registered in the cell list are stored in list memory 11, and when the value of the register reaches "27", then it returns to "0". When sequencer 12 stores the cell data of all cells to be registered in the cell list in list memory 11, then sequencer 12 stores the cell data of the central data in the central cell data storage unit (step S5).

Then, sequencer 12 extracts a leading particle or a central particle from the central cell, and controls memory controller 20 to read the particle data of the leading particle or the central particle from storage unit 30, and to transfer the read particle data to force calculator 40 (step S6). Based on the cell data of the central cell, sequencer 12 sets the fourth counter that counts the number of particles in the central cell to "n" which is equal to the number of particles in the central cell (step S7), and sets the fifth counter that counts the number of cells registered in the cell list to "27" which represents the number of cell data in the cell list (step S8).

Then, sequencer 12 selects one of the central cell and the surrounding cells registered in the cell list, reads the cell data of the selected cell from list memory 11 (step S9), and controls memory controller 20 to read the particle data of the particles contained in the cell from storage unit 30 and to transfer the read particle data to force calculator 40 (step S10). Force calculator 40 calculates short-range forces acting on the leading particle or the central particle by using the particle data of the leading particle or the central particle which has been transferred previously and the particle data of the particles which has been transferred subsequently that are contained in the selected cell. It is next determined whether or not the particle data of all the particles contained in the selected cell have been transferred to force calculator 40 (step S11). If the particle data of all the particles have not been transferred to force calculator 40, then control goes back to step S10 to repeat the process of transferring the particle data to force calculator 40.

When transfer of the particle data of all the particles contained in the selected cell to force calculator 40 is completed, sequencer 12 decrements the value of the fifth counter that counts the number of cells registered in the cell list by "1" (step S12), and determines whether or not the value of the fifth counter is "0" in order to determine whether or not the transfer of the particle data of all the cells registered in the cell list has been completed (step S13). If the value of the fifth counter is not "0", then control goes back to step S9. A cell, wherein the transfer of particle data has not been finished, is selected from the central cell and the surrounding cells registered in the cell list, and processing of steps S9 through S13 is performed on the selected cell.

At this time, the value of the register of sequencer 12 which stores the read address in list memory 11 is incremented by "1". When the cell data of all cells registered in the cell list are read and when the value of the register reaches "27", then it returns to "0".

If the value of the fifth counter is "0" in step S13, then the value of the fourth counter is decremented by "1" (step S14). Then, it is determined whether or not the value of the fourth counter is "0" in order to determine whether or not the calculation of short-range forces acting on all the particles contained in the central cell is finished (step S15). If the value of the fourth counter is not "0", then control goes back to step S6. A particle which has not served as a leading particle or as a central particle is selected, and processing of steps S6 through S15 is performed on the selected particle (new central particle).

If the value of the fourth counter is "0" in step S15, then the value of the third counter is decremented by "1" (step S16). Then, it is determined whether or not the value of the third counter is "0" in order to determine whether or not the movement of the central cell in the x direction is finished, i.e., whether the central cell has reached the end of the system (step S17). If the value of the third counter is not "0", then control goes back to step S5. A cell adjacent to the preceding central cell in the x direction is defined as a new central cell. Sequencer 12 controls memory controller 20 to read the cell data of the new central cell and the surrounding cells around the new central cell from storage unit 30, and to store the read cell data into list memory 11. Based on the updated cell list, processing of steps S5 through S17 is performed.

If the value of the third counter is "0" in step S17, then the value of the second counter is decremented by "1" (step S18). Then, it is determined whether or not the value of the second counter is "0" in order to determine whether or not the movement of the central cell in the x and y directions is finished, i.e., whether the central cell has reached the end of the system (step S19). If the value of the second counter is not "0", then control goes back to step S4. The value of the third counter is set to the number of divisions in the x direction, and processing of steps S4 through S19 is performed.

If the value of the second counter is "0" in step S19, then the value of the first counter is decremented by "1" (step S20). Then, it is determined whether or not the value of the first counter is "0" in order to determine whether or not the movement of the central cell in the x, y, and z directions is finished, i.e., whether the central cell has reached the end of the system (step S21). If the value of the first counter is not "0", then control goes back to step S3. The value of the second counter is set to the number of divisions in the y direction, and processing of steps S3 through S21 is performed. If the value of the first counter is "0" in step S21, then the processing sequence is ended.

The processing sequence shown in FIGS. 3 through 5 represents a process wherein all the cells serve as a central cell by moving the central cell from one end to the other end of the system in the x direction, moving the central cell in the same manner at each of the cell arrays in the y direction, and moving a cell plane lying in the x and y directions at each of the cell arrays in the z direction. However, the order in which the central cell moves in the x, y, and z directions is not limited to the above order, but may be any order insofar as the central cell moves to an adjacent cell in either one of the x, y, and z directions and insofar as all the cells successively serve as the central cell.

Figure 6:
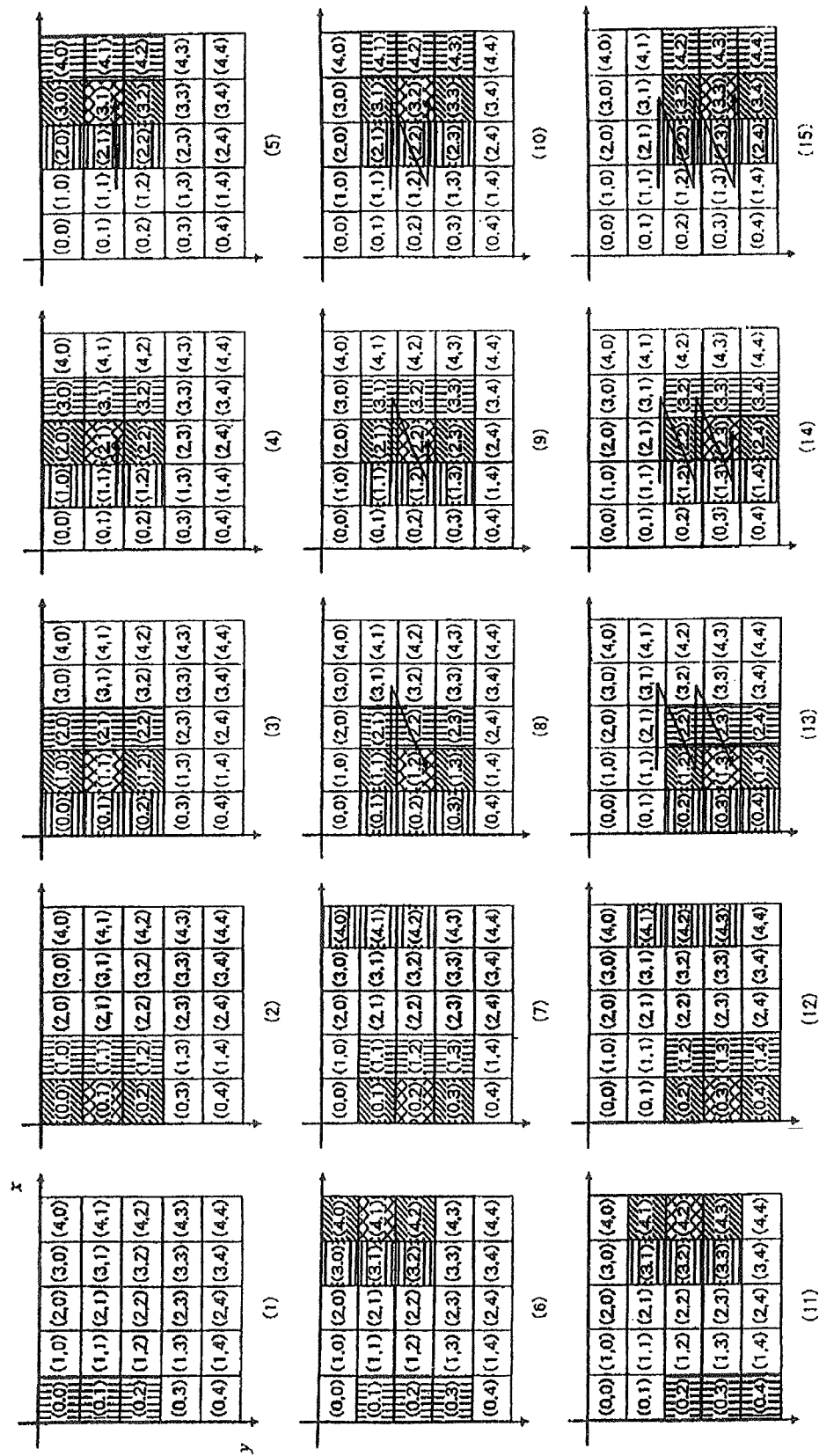
FIG. 6 is a diagram showing the manner in which a central cell moves according to the processing sequence shown in FIGS. 3 through 5.

FIG. 6 shows the manner in which the central cell to be calculated moves according to the above processing sequence. For the sake of brevity, the system is shown as being planar and divided into 5×5 cells=25 cells which are assigned corresponding coordinates (x, y). In the example shown in FIG. 6, short-range forces acting on particles are calculated with respect to 3×3 cells=9 cells.

Cell data of three cells (shown as vertically, obliquely, and horizontally hatched in FIG. 6) are read from storage unit 30 and registered in a cell list. Cell data to be read next are moved in the order of x=0, 1, 2, 3, 4 in the x direction. When an end (x=4) of the system in the x direction is reached, cell data to be read are shifted one cell in the y direction, and cell data to be read next are moved again in the order of x=0, 1, 2, 3, 4 in the x direction. In this case, the central cell moves from the cell represented by the coordinates (0, 1) to the cell represented by (4, 1), from the cell represented by the coordinates (0, 2) to the cell represented by (4, 2), from the cell represented by the coordinates (0, 3) to the cell represented by (4, 3), and from the cell represented by the coordinates (0, 4) to the cell represented by (4, 4) as indicated by the cross-hatched cells in FIG. 6.

In FIG. 6, the central cell is moved by scanning the cells in the x direction and then shifting the cell data by one cell at a time in the y direction. Insofar as all the cells can serve as a central cell, however, the central cell may be moved by scanning the cells in the y direction and then shifting the cell data by one cell at a time in the x direction.

By using the many-body calculating apparatus according to the present invention, since the central cell is successively moved to adjacent cells, the cell data of some surrounding cells can be shared when the cell list is updated as the central cell is moved. Therefore, the process of reading the cell data of the surrounding cells from storage unit 30 to list memory is shortened. Accordingly, the time required to update the cell list is reduced. As described above, because sequencer 12 determines a central cell to be calculated next and surrounding cells according to the predetermined rules, the cell list can be autonomously updated by sequencer 12. Therefore, short-range forces acting between particles can be efficiently calculated.

The many-body calculating apparatus according to the present invention employs the addresses of storage unit 30 where the information of the leading particle is stored as identification information for identifying cells, and employs only the addresses and the number of particles contained in a cell as cell data. Consequently, the amount of data stored in storage unit 30 and list memory 11 is smaller than in the case of conventional many-body calculating apparatuses. The storage unit of the many-body calculating apparatus may thus have a reduced storage capacity, and hence the many-body calculating apparatus may be less costly to manufacture.

While a preferred embodiment of the present invention has been described using specific terms, such description is for illustrative purposes only, and it is to be understood that changes and variations may be made without departing from the spirit or scope of the following claims.

What is claimed is:

1. An apparatus for calculating short-range forces between particles contained in a system, the apparatus comprising:
   a force calculator for calculating the short-range forces using particle data representing data of particles which are required to calculate the short-range forces;
   a storage unit for storing particle data of all particles contained in the system and cell data of respective cells representing spaces which are produced by dividing said system, said cell data including information to identify said cells and information representing the number of particles in said cells;
   an address generator for holding a cell list representing cell data of a central cell containing a central particle to be calculated for the short-range forces and a predetermined number of surrounding cells that are present around the central cell, for designating particle data of the central particle and particles that are present around the central particle, said particle data being used to calculate said short-range forces, from the cell data represented by said cell list, and for successively updating said cell list according to predetermined rules each time the calculation of short-range forces between each of all the particles in said central cell and the particles that are present around the central particle is completed, until each of the cells in the system has served as a central cell; and
   a memory controller for reading the particle data of the central particle and the particles that are present around the central particle that have been designated by said address generator, from said storage unit, and transferring the read particle data to said force calculator.

2. The apparatus according to claim 1, wherein said address generator establishes a cell which is adjacent to the central cell contained in the cell list which is to be updated, in either the x, y, or z directions of said system, as a central cell contained in the cell list which has been updated.

3. A method of calculating short-range forces between particles contained in a system, the method comprising
   storing, in a first storage unit, particle data representing data of the particles which are required to calculate the short-range forces, and cell data of respective cells representing spaces which are produced by dividing said system, said cell data including information to identify said cells and information representing the number of particles in said cells;
   holding, in a second storage unit, a cell list representing cell data of a central cell containing a central particle to be calculated for the short-range forces and a predetermined number of surrounding cells that are present around the central cell;
   designating particle data of the central particle and particles that are present around the central particle, said particle data being used to calculate said short-range forces, from the cell data represented by said cell list;
   reading by using a memory controller the designated particle data from said first storage unit and transferring the read particle data to a force calculator for calculating short-range forces between particles; and
   successively updating said cell list according to predetermined rules each time the calculation of short-range forces between each of all the particles in said central cell and the particles that are present around the central particle is completed, until each of the cells in the system has served as a central cell.

4. The method according to claim 3, further comprising:
   establishing a cell which is adjacent to the central cell contained in the cell list which is to be updated, in either the x, y, or z directions of said system, as a central cell contained in the cell list which has been updated.

5. An address generator for designating particle data of particles to calculate short-range forces between particles contained in a system, to be supplied to a force calculator for calculating the short-range forces using particle data representing data of the particles which are required to calculate the short-range forces, the address generator comprising:
   a list memory for holding, as a cell list, cell data of respective cells representing spaces which are produced by dividing said system, said cell data including information to identify said cells and information representing the number of particles in said cells, said cells including a central cell containing a central particle to be calculated for the short-range forces and a predetermined number of surrounding cells that are present around the central cell; and
   a sequencer for designating particle data of the central particle and particles that are present around the central particle, said designated particle data being used to calculate said short-range forces, from the cell data represented by said cell list, and for successively updating said cell list according to predetermined rules each time the calculation of short-range forces between each of all the particles in said central cell and the particles that are present around the central particle is completed, until each of the cells in the system has served as a central cell.

6. The address generator according to claim 5, wherein said sequencer establishes a cell which is adjacent to the central cell contained in the cell list which is to be updated, in either the x, y, or z directions of said system, as a central cell contained in the cell list which has been updated.

7. A method of generating addresses by designating particle data of particles to calculate short-range forces between particles contained in a system, to be supplied to a force calculator for calculating the short-range forces using particle data representing data of the particles which are required to calculate the short-range forces the method comprising:
   holding, as a cell list in a storage unit, cell data of respective cells representing spaces which are produced by dividing said system, said cell data including information to identify said cells and information representing the number of particles in said cells, said cells including a central cell containing a central particle to be calculated for the short-range forces and a predetermined number of surrounding cells that are present around the central cell; and designating by using a sequencer, particle data of the central particle and particles that are present around the central particle, said designated particle data being used to calculate said short-range forces, from the cell data represented by said cell list, and successively updating said cell list in said storage unit according to predetermined rules each time the calculation of short-range forces between each of all the particles in said central cell and the particles that are present around the central particle is completed, until each of the cells in the system has served as a central cell.

8. The method according to claim 7, further comprising:
establishing a cell which is adjacent to the central cell contained in the cell list which is to be updated, in either the x, y, or z directions of said system, as a central cell contained in the cell list which has been updated.

* * * * *